United States Patent

Fitzky et al.

[11] 4,203,067
[45] May 13, 1980

[54] APPARATUS FOR DETERMINING THE WATER CONTENT OF ISOTROPIC MATERIALS BY MEANS OF MICROWAVE ABSORPTION

[75] Inventors: Hans G. Fitzky, Odenthal-Hahnenberg; Franz Schmitt, Cologne; Norbert Bollongino, Leichlingen; Helmut Rehrmann, Leverkusen, all of Fed. Rep. of Germany

[73] Assignee: Bayer Aktiengesellschaft, Leverkusen, Fed. Rep. of Germany

[21] Appl. No.: 886,693

[22] Filed: Mar. 15, 1978

[30] Foreign Application Priority Data

Mar. 30, 1977 [DE] Fed. Rep. of Germany ....... 2714094

[51] Int. Cl.$^2$ .............................................. G01R 27/04
[52] U.S. Cl. ............................ 324/58.5 C; 324/58.5 B
[58] Field of Search ................... 324/58.5 C, 58.5 B, 324/58 C, 58 B, 58 R

[56] References Cited

U.S. PATENT DOCUMENTS

| | | | |
|---|---|---|---|
| 3,080,520 | 3/1963 | O'Reilly et al. | 324/58 C X |
| 3,448,379 | 6/1969 | Rosenbaum | 324/58 C |
| 3,883,798 | 5/1975 | Free | 324/58.5 C |
| 4,050,015 | 9/1977 | Zollner | 324/58.5 C |

FOREIGN PATENT DOCUMENTS

| | | | |
|---|---|---|---|
| 2324735 | 11/1973 | Fed. Rep. of Germany | 324/58.5 C |
| 1334791 | 10/1973 | United Kingdom | 324/58.5 C |

*Primary Examiner*—M. Tokar
*Attorney, Agent, or Firm*—Sprung, Felfe, Horn, Lynch & Kramer

[57] ABSTRACT

The measuring arrangement consists of a frequency-modulated microwave oscillator which supplies a closed resonator charged with the sample in a transmission circuit. The change in the quality factor induced by the water content of the sample is used as the unknown. The sample is located in the substantially homogeneous range of the electrical field maximum of a stationary wave in a cylindrical single mode cavity resonator of the $E_{010}$ mode, the diameter of the sample being not more than 25% of the internall diameter of the resonator and the length of the sample being not more than 50% of the height of the resonator.

8 Claims, 2 Drawing Figures

APPARATUS FOR DETERMINING THE WATER CONTENT OF ISOTROPIC MATERIALS BY MEANS OF MICROWAVE ABSORPTION

The invention relates to an apparatus for determining the water content of electrically non-conductive powders, granulates, pastes and other isotropic materials. The apparatus consists of a frequency-modulated microwave oscillator which feeds a closed resonator charged with the sample in a transmission arrangement, and an instrument for measuring the change in quality of the resonator induced by the sample.

It is important to be able to determine quickly the water content of powders, granulates, pastes and fibrous material for large-scale production of these materials. Examples of such materials include pharmaceutical products, plastics granulates, raw materials for washing agents and finished products, building materials and ceramic pre-products and agricultural produce.

In order to monitor the industrial production and processing of these products, it is necessary to use a fast-operating measuring instrument whose results may be used, inter alia, for controlling operation or for quality control during final inspection.

Apparatuses described in the literature for measuring the water content of bulk materials, pastes etc. are usually designed as free-jet apparatuses which are provided for monitoring continuously moving material and which only give relatively inaccurate results owing to the varying bulk density and reflection of the measuring jet, or whose design is not suitable for rapid and precise routine measurement in operating laboratories (German Offenlegungsschrift No. 2,017,061 and German Offenlegungsschrift No. 2,309,278). Microwave moisture-measuring instruments for powdery or granular products are described in the "GIT-Fachzeitschrift für das Laboratorium" 1974 Volume, pages 869–880 and pages 994–1000. The change in quality of the resonator due to the sample is used as the unknown. The resonator is fed by a frequency-modulated microwave oscillator. The frequency deviation in this case is large enough to cover completely the resonance curve of the resonator both when empty and when full of sample. Downstream of the transmission resonator is located a microwave detector whose direct voltage signal gives a direct measure for the moisture of the material. However, when operating with such an apparatus, the accuracy of measurement has been found to vary greatly. It has been found that the accuracy depends upon the quantity of sample. Moreover, it has been found that even slight variations in the bulk density of the product influence the measured result significantly. The last-mentioned effect interferes particularly when such apparatus are used in the laboratory as routine measuring apparatus.

An object of the invention is to improve the arrangement described at the beginning so that it is suitable for examining small quantities of isotropic material with moisture contents in the residual moisture range, i.e. quantities of from 0.1 to 5 g containing from 0.01 to 0.5 percent by weight of $H_2O$. The accuracy of measurement is to be as great as possible even with varying quantities of sample, without slight variations in the bulk density influencing the measured result to a significant degree.

According to the invention there is provided an apparatus for measuring the water content of a sample of an electrically non-conductive isotropic material, comprising a closed, cylindrical, single mode, cavity resonator adapted to be excited in the $TM_{010}$ mode a frequency-modulated microwave oscillator for supplying microwave energy to the resonator, a sample container located in the substantially homogeneous range of the electrical field maximum of a stationary wave in the resonator, the diameter of the sample being not more than 25% of the internal diameter of the resonator and the length of the sample being not more than 50% of the length of the resonator, and an instrument for determining the change in quality of the resonator indicated by the sample by measuring microwave energy transmitted therethrough.

A microwave cavity resonator is preferably used as resonator, whose magnification factor (number of irradiations) may easily be regulated in the range of between 20 and 20,000, thus ensuring adaptation to the desired range of moisture measurement. Finely particulate materials, pastes, crimped fibres etc., containing residual amounts of moisture may be measured satisfactorily in quantities of up to 6 g using this arrangement. Higher moisture contents may be measured by reducing the quality of the resonator or by reducing the volume of sample. Generally speaking, moisture values of a maximum of 20% by weight may be measured well using a measuring arrangement. Coarser powders or granulates (grain diameter from 1 mm) require greater measured volumes to determine a representative moisture content (for example from 0.1 to 1 liter).

The single mode cavity resonator preferably has iris diaphragms on its cylinder casing for magnetic coupling in and out.

The sample container preferably consists of a hollow cylindrical polytetrafluoraethylene (PTFE) body arranged axially and in the centre of the resonator and supported by guide rings above and below the volume of sample in an axial protective tube composed of quartz glass or a similar low-loss material hoving a low water-absorbing capacity. This protective tube also contributes to the homogenization of the electric field at the sample position and penetrates the cylindrical resonator over its entire height.

An embodiment of the invention is characterised by the fact that a microwave oscillator is used for supplying the measuring arrangement and the frequency deviation of the microwave oscillator is limited so that the complete resonance curve of the measuring resonator charged with the full or empty sample container is covered while there is no excitation when the measuring resonator is empty. The frequency range used in practice lies between 2 and 30 GHz, the frequency deviation being between 10 and 1000 MHz and the modulation frequency being between 1 Hz and 100 kHz. The transmission signal and thus the microwave absorption which depends upon the product are preferably measured using a differential connection which forms the difference between the rectified microwave signals at the imput of the resonator (the reference signal) and the rectified microwave signal at the output of the resonator (the transmission signal) and displays the result digitally.

The principal advantage of the invention is that an almost uniformly high degree of accuracy of measurement is obtained even when the bulk density of the powdery product varies in the measurement cell. A typical accuracy of measurement and reproducibility may be ±0.5% of the measured value.

The invention is described in more detail below with reference to the accompanying drawings, in which.

Figure 1:
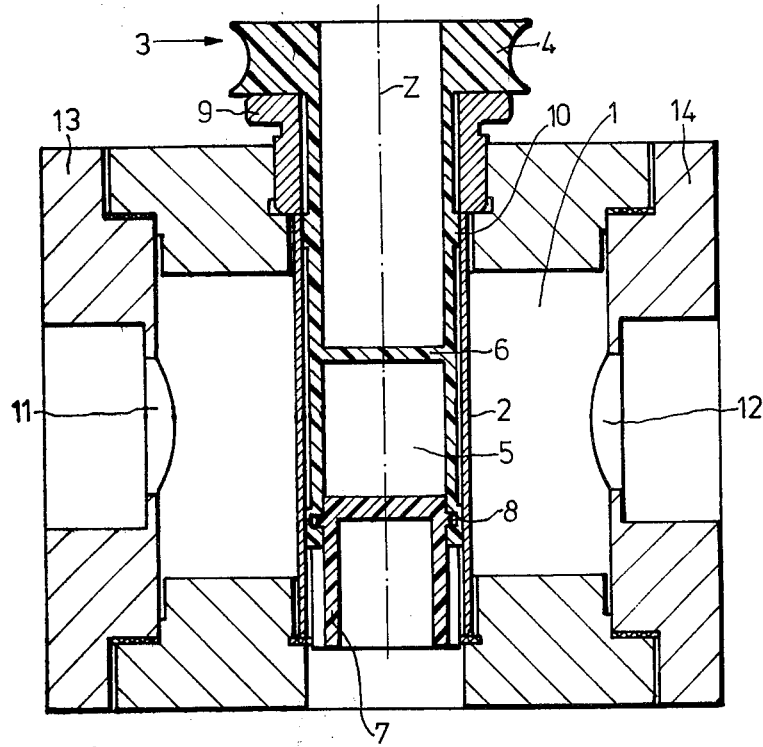
FIG. 1 shows a resonator measurement cell with a sample container.

The single mode resonator in FIG. 1 comprises a cylindrical cavity 1 in which the cylindrically symmetrical $TM_{010}$ mode is excited. A quartz tube 2 for receiving the sample container 3 is placed in the centre of the resonator so that the axis of the sample container coincides with the axis Z of the resonator. For this purpose, the resonator is provided with corresponding openings for inserting the sample container. The sample container 3 consists of a PTFE tube having a lid or handle 4 at its upper end. The actual sample chamber 5 is limited at the top by a partition 6 and at the bottom by a closure member 7. The closure member 7 serves to close the sample chamber 5 and is provided with a bayonet fitting 8 for this purpose. In order to fill the sample container 3, the sample container 3 is placed, with its lid 4, on a balance and a constant amount of powder is weighed into the chamber 5 in each case. The closure member 7 is then inserted and the sample container 3 is introduced into the resonator 1. Stops 9 ensure exact positioning in the axial direction. Guide rings 10 prevent the sample container from tipping laterally. The volume of the sample chamber 5 is such that its diameter is not more than 25% of the internal diameter of the resonator and its length is not more than 50% of the height of the resonator.

The resonator 1 is coupled in and out by opposing iris diaphragms 11 and 12 in the cylinder casing 13, 14. The Q-factor of the resonator and thus the number of irradiations may easily be regulated in the range between 20 and 20,000 by suitable selection of the diameter of the iris diaphragms 11 and 12. The measuring arrangement may be adjusted to the desired range of moisture measurement in this way, and in order to fill the sample container 3, corresponding PTFE inserts may be used for smaller amounts of sample, if necessary.

A typical diameter of the sample chamber 5 is 2 cm and a typical length is 2.5 cm. Finely particulate materials, pastes and crimped fibres may be measured at a measurement frequency of 2.5 GHz in quantities of up to about 6 g, where they contain a residual amount of moisture. Higher moisture contents may be detected by reducing the volume of sample and using corresponding PTFE inserts for smaller quantities of sample if it is not sufficient to reduce the number of irradiations (reduction of the resonator quality).

Figure 2:
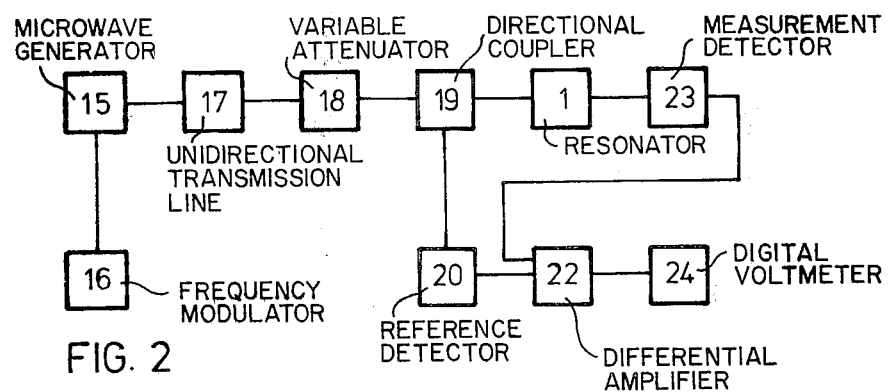
FIG. 2 is a block diagram for a microwave moisture-measuring instrument using the resonator measurement cell.

FIG. 2 is a block diagram of the microwave circuit for the measuring arrangement. The measuring apparatus is fed by a microwave frequency-modulated by a generator 15 and modulator 16. The accuracy of measurement is determined by the choice of generator frequency in addition to the factors mentioned above. The frequency is in the range of the maximum of the water band, the position of the maximum being determined by the temperature and the strength of the bands of the water. In this context, reference should also be made to the possibility of minimizing the effect of the temperature on measurement by selecting a frequency which is suitable for a specific temperature interval. The microwave absorption, for example of free water at 9.3 GHz at from 10° to 30° C. (absorption value at 10° C. taken as 100) falls from 100 to 68 while it increases from 100 to 113 at 24 GHz. The maximum absorption lies at 9.3 GHz at about 0° C. and at 24 GHz at about 30° C. In general, higher temperatures shift the absorption maximum to higher frequencies (there is a shorter relaxation period of the water dipole). A stronger combination of the water dipole, for example in a very polar matrix, leads to a reduction of the frequency of the absorption maximum. For this reason, the residual moisture is preferably measured at lower frequencies than high water contents of above between 5 and 15% by weight. The displacement of the absorption to lower frequencies in the range of the residual moisture may be explained by a relatively strong bonding of water in this case.

The frequency-modulated microwave radiation of the osicillator 15 is fed to the resonator 1 (the measurement cell) via a unidirectional transmission line 17, a variable attenuator 18 and a directional coupler 19. The reference intensity $I_0$ at the input of the transmission resonator 1 is branched off via the loosely coupled directional coupler 19 and is fed to a differential amplifier 22 after rectification by a reference detector 20. The measurement detector 23 acting as a rectifier is arranged downstream of the resonator. The direct current output signals from reference detector 20 and the measurement detector 23 are fed to the differential input of the differential amplifier 22 whose output signal is displayed by a digital voltmeter 24. The average frequency and frequency deviation of the oscillator 15 (for example 2.6 GHz, deviation about ±0.2 GHz, modulation frequency about 220 Hz) are regulated in such a way that the resonance curve of the resonator 1 is completely covered when the sample container 3 is inserted and filled, but excitation does not take place when the sample container is removed. The measurement detector 23 does not therefore receive a signal at the output of the resonator 1 so that the display of the digital voltmeter 24 may be used for regulating a constant microwave intensity at the input of the resonator 1 by means of the attenuator 18. As a result, variations in the output of the generator may be compensated or measurement may be carried out by zero adjustment. Zero transmission and 100% transmission of the apparatus may be controlled and adjusted by filling the sample container with an absorbant material (for example, suitable plastics cylinder filled with water) and by introducing the empty sample container. Glass cylinders of different types of glass and different diameters which are inserted in tight-fitting PTFE bodies may be used as standards for test points within the measuring range.

A filling composed of a two-component epoxy resin containing 60% of silicon powder, for example, has proved suitable as a standard substance for the 100% value, apart from 100% water. Glass bodies composed of Jena glass or other inorganic glasses of different diameters encapsulated in suitable PTFE bodies are preferably used as standard points within the measurement range.

At the beginning of the measuring process, the sample container 3 is filled with a weighed quantity of the material and is inserted in the resonator 1. The peak amplitude of the resonance curve, the magnitude of which is a monotonic function of the water content of the sample, serves as measured value of the microwave absorption. The measured value is formed by the differential amplifier 22. The frequency deviation of the oscillator is regulated in such a way that the resonance curve of the measurement cell 1 charged with samples of different moisture contents is completely covered so that the amplitude of the oscillator 15 remains constant in the entire range of frequency (AM proportion 2%). Accuracy of measurement and reproducibility of up to ±0.5% of the measured value may be obtained.

What we claim is:

1. An apparatus for measuring the water content of a sample of an electrically non-conductive isotropic material, comprising:
   a cylindrical single mode transmission cavity resonator excitable in the $TM_{010}$ mode and having protective tube extending centrally axially through the entire resonator cavity perpendicular to the direction of microwave propogation, the tube being open and accessible at both ends and composed of a dielectric material having a low water absorbing capacity and contributing to the homogeneity of an electric field in the resonator center;
   a sample container including a sample chamber for holding the sample to be measured and configured to be insertable into the protective tube through one end thereof, the sample chamber having a diameter of not more than 25% of the diameter of the resonator cavity and a height of not more than 50% of the height of the resonator cavity;
   a frequency modulated microwave oscillator for supplying microwave energy to the resonator; and
   detector means for receiving microwave energy transmitted from the resonator to effect measuring of the water content of a sample in the resonator.

2. An apparatus according to claim 1, wherein the resonator has iris diaphragms in its cylindrical wall for coupling microwave energy in and out of the resonator.

3. An apparatus according to claim 1 or 2, wherein the sample container comprises a hollow cylindrical body of polytetrafluoroethylene arranged axially and in the centre of the resonator when inserted in the protective tube and supported by guide rings above and below the volume of sample in the axially extending protective tube.

4. An apparatus according to claim 3, wherein the protective tube is composed of quartz.

5. An apparatus according to claim 1, wherein the frequency deviation of the microwave oscillator is such that the complete resonance curve of the resonator charged with the filled or empty sample container is covered while there is no excitation when the resonator is empty.

6. An apparatus according to claim 1, wherein the frequency of the microwave oscillator is between 2 and 30 GHz, the frequency deviation is between 10 and 1000 MHz and the modulation frequency is between 1 Hz and 100 kHz.

7. An apparatus according to claim 1, wherein the detector means comprises a difference circuit for forming the difference between rectified microwave signals at the input and output of the resonator.

8. An apparatus according to claim 7, wherein means are provided for displaying the result digitally.

* * * * *